(12) United States Patent
Yianni

(10) Patent No.: US 6,521,283 B1
(45) Date of Patent: Feb. 18, 2003

(54) NON-THROMBOGENIC SURFACES

(75) Inventor: Yiannakis Petrou Yianni, Uxbridge (GB)

(73) Assignee: Biocompatibles Limited, Middlesex (GB)

( * ) Notice: Subject to any disclaimer, the term of this patent is extended or adjusted under 35 U.S.C. 154(b) by 0 days.

(21) Appl. No.: 08/064,052

(22) PCT Filed: Oct. 22, 1991

(86) PCT No.: PCT/GB91/01846

§ 371 (c)(1),
(2), (4) Date: May 18, 1993

(87) PCT Pub. No.: WO92/06719

PCT Pub. Date: Apr. 30, 1992

(30) Foreign Application Priority Data

Oct. 22, 1990 (GB) .............................. 9022938

(51) Int. Cl.$^7$ ................................ B05D 5/00
(52) U.S. Cl. .................. 427/2.1; 427/2.28; 427/2.3; 424/422
(58) Field of Search .......................... 427/2, 2.1, 2.24, 427/2.25, 2.28, 2.3; 514/78, 76; 523/112; 424/422, 423, 424; 428/195, 409, 411.1, 412, 500, 522

(56) References Cited

U.S. PATENT DOCUMENTS

| | | | | |
|---|---|---|---|---|
| 2,576,576 A | | 11/1951 | Cresswell et al. | |
| 3,756,238 A | | 9/1973 | Hanke | 128/270 |
| 4,091,170 A | | 5/1978 | Godfrey | 428/510 |
| 4,451,425 A | | 5/1984 | Meyer | 264/300 |
| 4,634,727 A | | 1/1987 | Kamikaseda et al. | 524/145 |
| 4,798,593 A | | 1/1989 | Iwatschenko | 604/164 |
| 4,828,561 A | * | 5/1989 | Woodroof | 623/8 |
| 4,865,984 A | * | 9/1989 | Nemerson et al. | 435/288 |
| 5,063,090 A | * | 11/1991 | Wannlund | 427/384 |
| 5,118,524 A | * | 6/1992 | Thompson et al. | 427/2 |
| 5,217,743 A | * | 6/1993 | Farah | 427/2 |
| 5,282,850 A | * | 2/1994 | Davidson | 623/3 |

FOREIGN PATENT DOCUMENTS

| | | |
|---|---|---|
| EP | 0032622 | 7/1981 |
| EP | 0157469 | 10/1985 |
| WO | WO 85/03295 | 8/1985 |
| WO | WO 90/09384 | 8/1990 |
| WO | WO 91/00745 | 1/1991 |

OTHER PUBLICATIONS

O. Larm et al., Progress in Artificial Organs (1985) 313–318 (no month).
C. Arnander et al., Journal of Biomedical Materials Research (1986) 20–235 to 246 (no month).
C. Arnander et al., Biomaterial (1987) 8, 496 to 499 (no month).
O. Larm et al., Biomaterial, Med. Dev. Art. Org., (1983) 11 (2&3), 161 to 173 (no month).
R. Larsson et al., Thrombosis Research (1980) 19, 43 to 54 (no month).
R.P. Quintana et al., Thrombosis Research (1981) 24, 379 to 395 (no month).
J. Hoffman et al., Carbohydrate Research (1983), 117, 328 to 331 (no month).
C. Esquivel et al., Surgery (1983), 95(1), 102–107 (no month).
H.L. Nossel et al., The Journal of Clinical Investigation (1974), 54, 43 to 53 (no month).
C. Arnander et al., Proc. Eur. Art. Org. (1982), 9, 312–321 (no month).
L.E. Lins et al., Proc. EDTA–ERA (1984) 21, 270 to 275 (no month).
K. Kodama et al., Thrombosis and Haemostasis (1987) 58(4) 1064 to 1067 (no month).
M. Ueno et al., Chem. Pharm. Bull. (1982) 30(12), 4570–4572 (no month).
L. Bindslev et al., Trans Am Soc. Artif. Intern Organs (1986) 32, 530–533 (no month).
D. Chapman et al., Biochemical Society Transactions (1989) 17, 951 to 953 (no month).
R. Larsson et al., Thrombosis Research (1979) 15, 157 to 167 (no month).
P. Olsson et al., Annals of the New York Academy of Sciences (1983) 525–537 (no month).
O. Larm et al., "Nonthrombogenic Surfaces, Prepared by End–Point Attachment of Heparin," 1 to 11, (date and source not known).
R. Larsson et al., "The Search for Thromboresistance using Immobilised Heparin." (date and source not known).
Kobunshi Robunshu, 39(4), pp. 197–202 (Apr. 1982), K. Tatebe et al.
Bird, R. et al "Material thrombelastography: . . . " Thrombosis Research, 51: 1988, pp. 471–483 (no month).
Bonte, F. et al "Interactions of polymerizable . . . " Biochim. et Biophys. Acta, 900 (1987), pp. 1–9 (no month).
Aviram, M. et al, Metabolism, 38: 343–7 (1989) (no month).
Kobayashi, T. et al, Biochim. et Biophys. Acta, 817: 307–312 (1985) (no month).
Hayward, J.A. et al, Ann. N.Y. Acad. Sci., 446:267–281 (1985) (no month).

\* cited by examiner

*Primary Examiner*—Marie Yamnitzky
(74) *Attorney, Agent, or Firm*—Sughrue Mion, PLLC

(57) ABSTRACT

A process for coating a blood-contacting surface comprising applying a solution of a fatty acid diester of phosphatidyl choline in an organic solvent to the surface and removing the solvent, provides a non-thrombogenic coating of phosphatidyl choline di-ester to the surface. Material for use in a blood-contacting device having such a coating and a blood-contacting device having such a coating.

13 Claims, 1 Drawing Sheet

NON-THROMBOGENIC SURFACES

Figure 1:
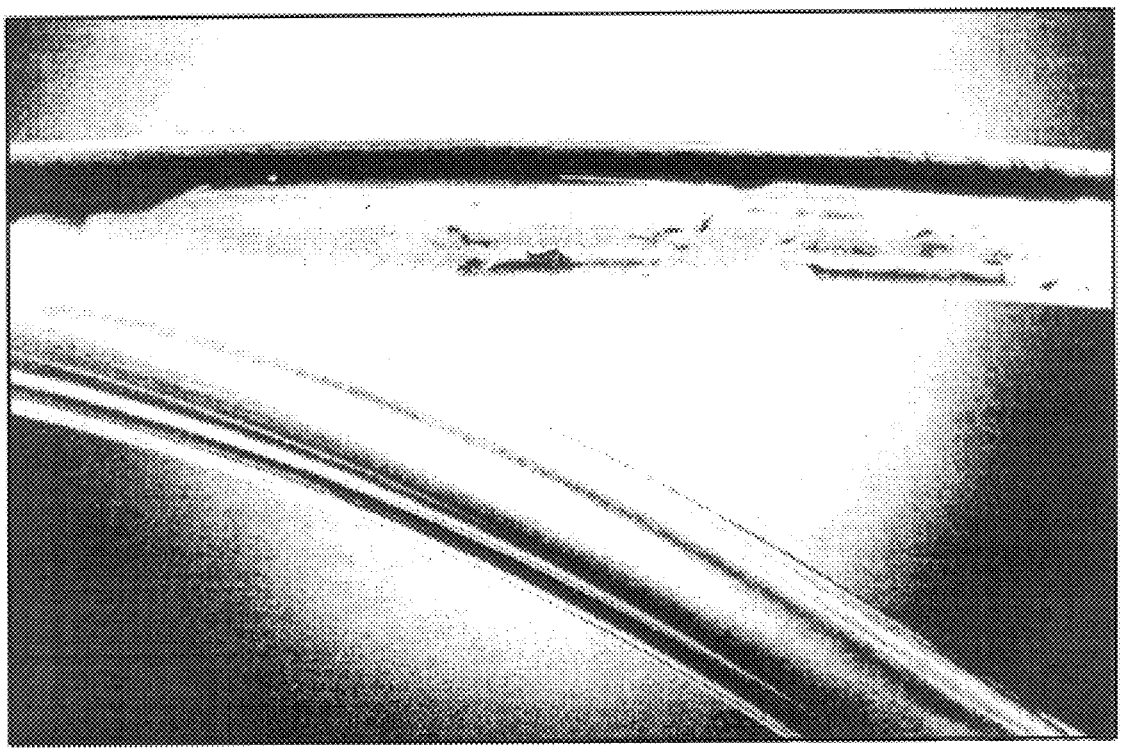

The present invention relates to the treatment of the surfaces of blood-contacting materials and devices to reduce the thrombogenicity of the materials.

Many modern surgical and other medical procedures, sampling techniques and test procedures involve the use of blood-contacting devices, such as catheters, drains and extracorporeal circuitry. These devices are used only once and then discarded for hygiene reasons and must therefore be constructed from the most economical materials available, usually polymeric plastics or glass. However glass and most synthetic and natural polymers tend to induce platelet aggregation and initiate the fibrinolytic clotting cascade leading to blockage of tubing and clogging of other apparatus such as filtration and dialysis membranes, interference with test procedures and, in certain cases, may have disastrous consequences for patients.

With existing technology, extra-corporeal circulation for haemodialysis, long term gas exchange at states of severe respiratory failure and cardiac support, e.g. after cardiac surgery, all require systemic heparinisation. Owing to the risk of excessive bleeding after systemic anticoagulant treatment many patients are disqualified for possible therapeutic measures. Likewise, commercial catheter sensors, e.g. for continuous determination of arterial oxygen, carbon dioxide tension, and of pH in the critically ill patient require systemic heparinisation to prevent microclotting on the sensor membranes and failure of the device.

It has been suggested that heparinisation of apparatus, particularly involving end point attachment of heparin fragments, will result in anti-thrombogenic coating of surfaces and thereby overcome the need for systemic heparinisation. Thus a method was developed in which heparin was coupled by end point attachment [Hoffman, J. et al., *Carboyhdr, Res.*, 117:328(1983), Larm, O. et al., *Biomat. Med. Dev. Art. Org.*, 11:161(1983)]. The resulting surfaces adsorbed antithrombin and large amounts of thrombin which were rapidly inhibited in the presence of antithrombin [Pasche, B, et al., *Thromb. Res.*, 44 739(1986)]. It is interesting to note that end-point attached heparin and the endothelium behave both quantitatively and qualitatively alike with respect to the inhibition of thrombin in the presence of plasma [Arnander C., et al., *J. Biomed. Mat. Res.*, 20:235(1986)] and that a polyethylene surface furnished with end-point attached heparin showed considerable capacity to inhibit Factor Xa [Kodama, K. et al. *Thromb. Haemostas.* (1987)].

Rigid polyethylene tubing sections with end-point attached heparin have been kept in the thoracic aorta of pigs for up to four months [Arnander C., et al., *Biomat. Res.*, (1987)]. When applied to vascular grafts of expanded polytetrafluoroethylene (PTFE) and to polyurethanes and implanted in the arteries of the sheep [Esquivel, C. O.et al., *Surgery*, 95:102(1984)], the end-point attached heparin surface substantially reduced the platelet and fibrin deposition.

The extra-corporeal circulation of blood through surface-heparinised devices offered the possibility to discriminate between the role of platelets and the plasma coagulation system as the main determining factor for achieving thromboresistance. In these experiments, it was demonstrated that coatings with other sulfated polymers were as platelet compatible as the heparin coatings, but still thrombogenic. Using the radioimmunoassay for fibrinopeptide A [Nossel, H. L. et al., *J. Clin. Invest.*, 54:43(1974)] it was shown that only coatings on which the heparin molecules could interact with plasma constituents were able to prevent conversion of fibrinogen to fibrin on contact with blood [Larsson R. and Lindahl U. *Artif. Org.*, Vol 3. Suppl. Proc. of the second meeting of the Intern. Soc. Artif. Org., (1979); Larsson R., et al., *Thromb. Res.*, 19:43(1980); Larm, O. et al., *Biomat. Med. Dev. Art. org.*, 11:161(1983)].

Thus the presence of intact functional groups on the immobilised heparin appeared mandatory for achieving thromboresistance and heparin coatings on blood-contacting medical devices could eliminate hazardous systemic anticoagulant treatment.

Experimental haemodialysis has been performed on dogs without systemic heparinisation and with cellulose acetate hollow fibers filters with end-point attached heparin surfaces. The efficiency of the coating on the total extra-corporeal system was demonstrated by the fact that the levels of fibrinopeptide A in the dialysed animals were not higher than in anaesthetised control animals with no surgery [Arnander C., et al., *Proc. Eur. Soc. Art. Org.*, 9:312(1982), Lins, L. E et al., *Proc. EDTA-ERA*, 21:270(1984). When end-point attached heparin surfaces were used in the extra-corporeal circuit, veno-venous by-pass for carbon dioxide elimination was easily performed for 24 h on dogs in a steady-state condition. After a small release of heparin, the coagulation system seemed unaffected as determined by fibrinopeptide A levels in the circulating blood [Larm, O. et al., An approach to antithrombosis by surface modification. Progress in artificial organs, ISAIO Press, Cleveland 1986, p313. Inacio, J. et al., Extracorporeal elimination of carbon dioxide using a surface heparinised vein-to-vein bypass system. EUROXY Workshop on design and techniques of extracorporeal gas exchange. Paris, Jun. 20, 1985. Bindsley L., et al., *Trans. Am. Soc. Art. Int. Org.* 32:530(1986).

Although heparinisation can reduce or prevent fibrinolytic clotting, this is at the expense of interference with the blood biochemistry, for instance the complexation of antithrombin and other subtle alterations. The heparinised surfaces are exerting many of the effects of heparin when administered as an anti-coagulant drug and the adverse side effects of heparin must, therefore, be taken into account when this technique is employed to improve haemocompatibility of blood-contacting devices.

Much effort has been devoted in recent years to the development of surface treatments, especially by covalent bonding of haemocompatible organic groups which improve the biocompatibility of blood-contacting surfaces and to the production of more biocompatible materials for use in blood-contacting devices such as surgical implants, prostheses and artificial hearts (see, for instance EP-A-0032 622 and EP-A-O 157 496). However, being intended to provide long term biocompatibility, these tend to be relatively expensive and are therefore less suitable for use in low-cost, single-use disposable devices.

The present invention provides a simple and cost effective means for reducing the thrombogenicity of blood-contacting surfaces using readily available materials.

The coatings of the present invention do not interfere with blood biochemistry in any manner and are therefore regarded as non-thrombogenic rather than as anti-thrombogenic. In addition to avoiding the side-effects of heparinisation, the present treatment offers the further advantages in many applications in that the coated surfaces have improved wetability and improved lubricity. This assists in, for instance, avoiding the formation of gas bubbles in tubing and facilitating insertion of catheters via surgical incisions.

According to the invention there is provided a process for coating a blood-contacting surface comprising applying a solution of a fatty acid diester of phosphatidyl choline in an organic solvent to the surface and removing the solvent.

FIG. 1 shows a comparison between a piece of medical tubing treated using the process of the invention and a similar tube of untreated medical tubing.

The surface to be treated may optionally be prepared for coating by washing to remove surface contaminants and, to improve the adhesion of the coating, by silylation or otherwise increasing the hydrophobicity of the surface.

The thickness of the coating will be selected according to the intended use of the blood-contacting device. Thus surfaces subjected to shear forces, such as tubing carrying a flow of blood, will generally receive thicker coatings than those for static applications such as sample phials or holders. The thickness of the coating will also be selected according to the intended duration of use of the coated device since thicker coatings will last longer. Typical thicknesses envisaged for coatings according to the invention are in the order of 1 to 1000 nanometres, preferably 10 to 500 nanometres and most preferably about 100 nanometres.

The blood-contacting surface may be a surface of a finished blood-contacting device or it may be the surface of a material to be used in forming a blood-contacting device. In the latter case subsequent forming steps are selected to avoid disrupting the coating formed by the process of the invention in blood-contacting portions of the device and to avoid chemical damage, for instance due to high temperatures, to the phosphatidyl choline ester. The surface being treated will hereinafter be referred to as the "substrate".

Substrates which may be coated according to the invention include glasses (eg soda glass and silica glass), metals such as silver, natural polymers, such as cellulose and semisynthetic cellulose derivatives, and artificial polymers such as polyurethanes (eg Pellethane), vinyl polymers such as polyvinyl chloride (PVC), polyesters such as polyethylene terephthalate (eg Dacron), polyalkenes such as polyethylene and polypropylene, polycarbonates and fluoropolymers such as polytetrafluoroethylene (PTFE) and other poly(fluoroalkenes) including fluorinated ethylene polymer (FEP) which is a copolymer of tetrafluoroethylene and hexafluoropropylene.

The fatty acid diesters of phosphatidyl choline which may be used in the process of the invention include esters of saturated and unsaturated fatty acids and may be pure single compounds such as dipalmitoyl phosphatidyl choline (DPPC) and dimyristoyl phosphatidyl choline (DMPC), mixtures of such compounds and purified natural products such as the fatty acid diesters of phosphatidyl choline from egg yolk or soya bean lecithin. Mixed diesters of phosphatidyl choline may be used. Preferably the fatty acid side chains will be straight as opposed to branched and will have from 12 to 20 carbon atoms. Purified natural products may contain a small proportion of components other than fatty acid diesters of phosphatidyl choline but these should not be present in sufficient amount to impair the thrombogenicity-reducing effect of the coating. In particular, phosphatidyl serine, and other anionic phospholipids which would cause clotting, should be avoided.

The solvent may be any conventional organic solvent which will dissolve the saturated fatty acid diester of phosphatidyl choline. Preferably the solvent will be selected for lack of toxicity and environmental hazards, for ease of removal, for compatibility with the material to be treated and for pharmacological acceptability. The solvent may be one which swells a polymeric substrate and this will aid the treatment process by permitting the phosphatidyl choline diester to penetrate the surface of the substrate. Alternatively the solvent may be selected to avoid swelling of a polymer substrate, particularly where there are fine dimensional tolerances to be maintained or other useful properties of the polymer would be thereby impaired.

Preferred solvents include the lower alkanols such as methanol, ethanol and iso- or n-propanol, halogenated alkanes such as chloroform and mixtures thereof. A particularly preferred solvent is a mixture of ethanol and chloroform, such as from 20:1 to 80:1 preferably 40:1 ethanol:chloroform by volume. Another preferred solvent is a mixture of Freon and ethanol such as from 50:50 to 99:1, preferably 90:10 Freon: ethanol by volume.

The concentration of phosphatidyl choline diester in the solvent will be selected to avoid use of unduly large quantities of solvent (and ensuing technical difficulties with removal thereof and economic penalties) whilst enabling efficient coating of the substrate. Preferred concentrations are in the range of from 0.5 to 20 mg/ml, preferably 2, 5 or 10 mg/ml.

The solution of phosphatidyl choline diester may be applied by any conventional coating technique such as immersion in a coating bath, spraying, painting or, for flat substrates, spin-coating, the coating conditions being varied according to the desired thickness of coating and the hydrophobicity of the substrate since the phosphatidylcholine diesters adhere more strongly to more hydrophobic substrates. Preferably coating is achieved by immersion of the substrate in a bath of a phosphatidyl choline fatty acid diester solution in a suitable solvent at an appropriate concentration and temperature for sufficient time to cover the surfaces to be coated.

The solvent may be removed by conventional techniques, preferably by evaporation under reduced or ambient pressure, in a gas stream and/or at elevated temperature. By careful selection of the solvent, concentration of the solution and coating and solvent-removal techniques, the thickness of the phosphatidyl choline diester coating may be controlled within a desired range.

Particularly preferred solvents, concentrations and coating and solvent removal techniques are described below and illustrated by the Examples.

Pre-washing of the surface may be effected using a suitable solvent such as those described above which may be the same as or different to the solvent or solvent system used to apply the coating. Pre-treatment of the surface by silylation is preferably effected using a reactive alkyl silane such as a halo silane, for instance trichlorooctadecyl silane or chlorodimethyl octadecylsilane in a suitable solvent such as hexane or chloroform. Excess reagent may be removed by a further washing step.

It will be appreciated that for some surfaces, such as glass, it will be necessary to pre-treat the surface for example by silylation to obtain a surface to which the fatty acid diester of phosphatidyl choline will adhere.

The present invention further provides a process for reducing the thrombogenicity of a blood-contacting surface comprising forming a coating on the surface of a fatty acid diester of phosphatidyl choline.

The invention also provides a material having a non-thrombogenic coating of a fatty acid diester of phosphatidyl choline on at least a portion of the surface thereof. Preferably the material is, or is a part of, a blood-contacting device. Typical blood contacting devices include tubing such as catheters, for instance central venous catheters, thoracic drain catheters, and angioplasty balloon catheters, tubing used in extracorporeal circuitry such as in heart and/or lung bypasses and entire extracorporeal circuits such as whole blood oxygenators, cannulae, vascular grafts, sutures, membranes such as those used in blood separation, apheresis and donorpheresis units, gas exchange membranes such as used in whole blood oxygenators, polycarbonate membranes and haemodialysis membranes and membranes used in diagnostic and biosensor devices, biosensors and other devices used in diagnosis such as cuvettes used in blood clotting time determinations. A particular example of a blood contacting device which may be treated according to the invention is a PVC thoracic drain catheter.

FIG. 1 shows a comparison between a piece of medical tubing treated by the process of the invention and a similar untreated piece of tubing. In each case the tubing has been exposed to a flow of blood. In the case of the untreated tube the formation of blood clots in the tube leading to blockage of the tube can be seen whereas the tube treated according to the invention is free of clots. Thus the presence of a non-thrombogenic surface inside the tube which was treated according to the invention is demonstrated.

The following Examples serve to illustrate the invention and are not intended to limit it in any way.

EXAMPLE 1

Treatment of PVC Tubing

Samples of hard and soft PVC tubing of the type which is used in extra-corporeal circuitry were either washed with warm ethanol or filtered deionised water and thoroughly dried prior to coating.

Both types of tubing were coated, in a dust free area to avoid contamination, by pipetting the coating solution (DPPC in ethanol (Analar) at 5 mg/ml or 1 mg/ml) into the hollow tube and gently working the solution backwards and forwards (for sections up to 120 cm in length) until the whole of the inside of the tubing was evenly coated.

Excess coating solution was then allowed to drain into a collection bath and the tubing allowed to dry at room temperature.

EXAMPLE 2

Treatment of Thoracic Drain Catheters

The type of thoracic drain catheter used in this example contained a frosted and a clear region and was made from PVC. The clear region is the part of the catheter which is normally inserted into the pericardium and contacts the body tissue. Coating of the two areas was carried out by separate processes as follows:

(a) Coating of Frosted Area

A 10 mg/ml solution of either DPPC or DMPC in ethanol was prepared and 3 ml pipetted into the interior surface of the catheter. The catheter was manually rotated in order that all of the region to be coated came into contact with the solution. Excess solution was allowed to drain out and the catheters were further treated by process (b) below.

(b) Coating of Clear Region

A 10 mg/ml solution of either DPPC or DMPC in chloroform was prepared and poured into a test tube. The clear end of the catheter was immersed in the solution for approximately 5 seconds and then quickly removed. The catheter was then air dried by hanging vertically for 24 hours.

EXAMPLE 3

Coating Polyester Yarn Suture Material

Samples of dyed and undyed braided polyester yarn suture material were washed in warm ethanol and air dried prior to coating. The washed and dried samples were coated by total immersion in a 10 mg/ml DPPC solution in ethanol, followed by air drying at room temperature after removal from the coating solution.

EXAMPLE 4

Spin-Coating

Petri-dishes (Sterilin polystyrene microbiological plates produced aseptically) were spun at 1500 r.p.m. and a 1 ml solution of either DPPC or DMPC in ethanol at concentrations of 10 mg/ml were applied to the spinning dishes using a Gilson 1 ml pipette. Samples were kept spinning for 30 seconds and then allowed to dry in air at room temperature.

Using the above method coatings were homogeneous as judged by surface analytical techniques.

EXAMPLE 5

Coating of Polvethylene Ribbon

Polyethylene (PE) ribbon was first washed in ethanol and dried. Material was then dipped briefly into ethanolic solutions of DPPC or DMPC (at 10 mg/ml concentration) and then air dried.

EXAMPLE 6

Coating of Polyethylene Ribbon

PE was silylated, prior to treatment with DPPC or DMPC to render the surface very hydrophobic, resulting in a layer of silane on which a very stable coating is formed. Silylation is carried out by immersion of the PE ribbon in a solution (0.01% w/v in hexane) of octadecyltrichlorosilane for 10 seconds, followed by air drying. The DPPC or DMPC coating is then applied according to Example 5.

EXAMPLE 7

Treatments of Polvyropvlene Hollow Fibre Membranes

Polypropylene hollow fibre membranes of the type used in oxygenators were first washed using Freon and dried prior to coating. DPPC solutions at 2 and 10 mg/ml were used to coat the material. In this case the DPPC was dissolved in a Freon/ethanol mixture (90:10 vol/vol).

The fibres were coated by slowly drawing them through a 'U'-shaped glass tube filled with the DPPC solution and allowed to air dry.

EXAMPLE 8

Treatment of IV Catheters

IV Catheters made of FEP (fluorinated ethylene polymer) were coated with DPPC using a dipping technique. DPPC was dissolved in ethanol at a concentration of 10 mg/ml and samples immersed in this solution for a few seconds. Catheters were air dried.

EXAMPLE 9

Treatment of Central Venous Catheters

An identical method to that of Example 8 was used to treat polyurethane (Pellethane) central venous catheters.

EXAMPLE 10

In Vitro Haemocompatibility Testing of Treated Materials

A quantitative platelet adhesion test was carried out by immersing samples in fresh citrated whole human blood at room temperature for 30 minutes. Tubing samples were prepared in 3 cm lengths sealed at both ends (the blood being introduced into the sample by hypodermic needle), and constantly mixed using a spiral mixer (tests were carried out in triplicate). Blood used in this assay was obtained using the double syringe method.

After incubation the samples were washed in isotonic phosphate buffered saline (PBS) and extracted into 1% trichloro acetate (TCA) (w/v) in 2 mM ethylene diamine tetraacetic acid (EDTA) to liberate ATP from any platelets adhering to the walls of the tubing.

The amount of ATP present in the extractant was estimated using the LKB Pharmacia ATP assay kit and a luminometer.

The number of platelets adhering to the samples was estimated from a standard curve using ATP levels associated with a known number of platelets.

The results for tubing coated according to Example 1 are recorded in Table 1:

TABLE 1

| | DONOR | | | | % |
|---|---|---|---|---|---|
| | 1 | 2 | 3 | $\overline{X}$ | Reduction |
| (a) HARD PVC | | | | | |
| Uncoated Control | 5.62 | 19.54 | 1.32 | 8.83 | — |
| Coated 5 mg/ml DPPC | 0.72 | 0.13 | 0.19 | 0.35 | 94 |
| Coated 10 mg/ml DPPC | 0.51 | 0.14 | 0.10 | 0.25 | 97 |
| (b) SOFT PVC | | | | | |
| Uncoated Control | 15.01 | 26.51 | 0.58 | 14.03 | — |
| Coated 5 mg/ml DPPC | 0.76 | 0.72 | 0.30 | 0.59 | 96 |
| Coated 10 mg/ml DPPC | 0.97 | 1.89 | 1.25 | 1.37 | 90 | results expressed as no. of platelets $\times 10^6$ per 3 cm lengths of tubing

Substantial reductions in platelet adhesion to coated PVC is observed indicating that there is a large reduction in the thrombogenicity of PVC tubing after coating with DPPC.

The results for catheters coated according to Example 2 are recorded in Table 2.

TABLE 2

| Sample | DONOR | | | | % |
|---|---|---|---|---|---|
| | 1 | 2 | 3 | $\overline{X}$ | Reduction |
| Frosted region (uncoated) | 6.83 | 4.61 | 7.45 | 6.30 | — |
| Frosted region/ 10 mg/ml DPPC | 0.88 | 1.05 | 0.59 | 0.84 | 87 |
| Frosted region/ 10 mg/ml DMPC | 0.31 | 0.11 | 0.56 | 0.33 | 95 |
| Clear region (uncoated) | 37.79 | 47.55 | 6.00 | 30.45 | — |
| Clear region/ 10 mg/ml DPPC | 0.53 | 1.38 | 0.60 | 0.84 | 97 |
| Clear region/ 10 mg/ml DMPC | 15.26 | 8.09 | 16.78 | 13.38 | 56.1 |

Results expressed as platelets adhered $\times 10^6$ per 3 cm lengths of catheters.

The results for petri dishes coated according to Example 4 are recorded in Table 3.

TABLE 3

| | DONOR | | | | % |
|---|---|---|---|---|---|
| | 1 | 2 | 3 | $\overline{X}$ | Reduction |
| Petri dish (Uncoated) | 47.43 | 50.23 | 56.92 | 51.52 | 0 |
| Petri dish (10 mg/ml DPPC) | 5.54 | 3.55 | 3.08 | 4.06 | 92 |
| Petri dish (10 mg/ml DMPC) | 1.20 | 0.26 | 3.78 | 1.75 | 97 |

Results expressed as no. of platelets $\times 10^6$ adhered per petri dish (50 mm diameter)

TABLE 4

| | DONOR | | | | % |
|---|---|---|---|---|---|
| | 1 | 2 | 3 | $\overline{X}$ | Reduction |
| Uncoated PE | 32.89 | 25.04 | 55.87 | 37.93 | — |
| DPPC-Treated PE (10 mg/ml) | 1.58 | 3.76 | 1.72 | 2.35 | 94 |
| DMPC-Treated PE (10 mg/ml) | 0.91 | 1.38 | 3.99 | 2.09 | 94 |

Results expressed as no. of platelets $\times 10^6$ per 22 mm$^2$ area of material The results for membranes treated according to Example 7 are shown in Table 5.

TABLE 5

| | DONOR | | | | % |
|---|---|---|---|---|---|
| | 1 | 2 | 3 | $\overline{X}$ | Reduction |
| Hollow Fibre | | | | | |
| Untreated | 4.08 | 4.07 | 16.95 | 8.36 | — |
| DPPC @2 mg/ml | 0.91 | 0.89 | 0.53 | 0.78 | 91 |
| DPPC @10 mg/ml | 0.41 | 10.08* | 0.52 | 3.67 | 56 |

*Result thought to be an outlier but included for completeness. Results expressed as no. of platelets $\times 10^6$ per 20 cm length of fibre.

The results for catheters treated according to Example 8 are shown in Table 6.

TABLE 6

| | DONOR | | | | % |
|---|---|---|---|---|---|
| | 1 | 2 | 3 | $\overline{X}$ | Reduction |
| Untreated Catheters | 4.10 | 9.36 | 11.98 | 8.48 | — |
| DPPC-treated Catheters (at 10 mg/ml in ethanol | 1.89 | 1.24 | 5.84 | 2.99 | 65 |

Results expressed as platelets $\times 10^6$ per 5 cm length of catheter

Central venous catheters treated according to Example 9, showed greater than 90% reduction in platelet adhesion.

EXAMPLE 11

In-Use Simulation

Three 15 cm segments of catheter (frosted region) coated according to Example 2 were prepared with the ends sealed using Eppendorf tubes. 40 ml of blood was collected from a female adult volunteer into tri-sodium citrate (32 g/l) using the double syringe technique (the first 5 ml were discarded). 2 ml of 0.025 M calcium chloride in 0.15 M sodium chloride was added to 10 ml of citrated blood. 4 ml of recalcified blood was then added to each of the three catheter segments. The tubes were placed in a 37° C. incubator for 150 minutes. The samples were turned every 30 minutes. After this incubation the blood was drained from each of the catheters. They were then rinsed using PBS to remove any loosely bound material. The results are as follows:

Untreated Frosted Region

When drained a small amount of plasma was obtained. There was a strongly adhered clot along the length of the catheter.

DPPC-treated Catheter Frosted Region

When blood drained easily. One small clot remained attached to the surface.

DMPC-treated Catheter Frosted Region

Whole blood drained easily. One small clot remained attached to the surface.

EXAMPLE 12

Haemocompatibility of Suture Materials

Samples of the braided material treated according to Example 3 were incubated in fresh, citrated whole blood as described in Example 10 above. After removal from the blood these materials were washed using PBS and prepared for scanning electron microscopy by fixing in an aliquot of the following solution:

2 ml 25% glutaraldehyde 83 ml 0.15 M PBS (pH 7.4) 15 ml saturated picric acid

The samples were washed in PBS and dehydrated using 70% ethanol, followed by absolute ethanol. Finally samples were sputter coated with gold (at 30 mA for 3 minutes) and observed under the electron microscope.

Results

Electron microscopy shows that the DPPC-coated materials adhere fewer blood cells than untreated materials and that platelet cells are not activated by the treated materials. The DPPC-coated materials therefore appear less thrombogenic than the untreated braided yarns.

EXAMPLE 13

Testing of the Spreading of Water on Treated Surfaces

A few drops of deionised water were applied to the coated surface using a pipette. With petri dishes coated according to Example 4, applied water drops spread completely over the surface showing that the coating rendered the normally very hydrophobic polystyrene extremely wettable.

EXAMPLE 14

Wettability of Treated Materials

The wettability of materials coated with DPPC according to the preceding examples was assessed by measurement of static contact angles using distilled water drops after 5 minutes in contact with the surface. The results were as shown in Table 7

| Material tested | Contact angles (°) (average) | Conclusion |
| --- | --- | --- |
| Soft PVC tubing (control) | 77, 71, 84, (77) | Non-wetting surface |
| Soft PVC tubing (coated as Ex. 1) | 9, <5, 10, (8) | Wettable surface |
| PVC thoracic drain catheter (control) | 76, 82, 70, (76) | Non-wetting surface |
| PVC thoracic drain catheter (coated as Ex. 2 at 10 mg/ml DPPC) | 26, 26, 19, (24) | Marked increase in wettability |
| Polyethylene (control) | 67, 80, 78, 76, (75) | Non-wetting surface |
| Polyethylene (coated as Ex. 5, at 10 mg/ml DPPC) | 12, 12, 21, (15) | Wettable surface |

What is claimed is:

1. A process for increasing the lubricity and reducing the thrombogenicity of a body tissue contacting surface of a single-use disposable device in which a portion of the surface of the device which is inserted into the body and contacts body tissue is subjected to the steps of:

a) coating of the portion with a solution of a fatty acid diester of phosphatidyl choline in an organic solvent; and b) removing the organic solvent to form a coating of the fatty acid diester of phosphatidyl choline physically adsorbed and retained on the portion by hydrophobic interaction, whereby the lubricity of the portion is increased and the thrombogenicity of the portion is decreased compared to an uncoated device.

2. The process of claim 1, wherein the solution comprises 2–10 mg/ml of the fatty acid diester of phosphatidyl choline.

3. The process of claim 1, wherein the solution consists of the solvent and the fatty acid diester of phosphatidyl choline.

4. The process of claim 1, wherein the portion of the surface of the device is formed of a plastic material.

5. The process of claim 4, wherein the plastic material is selected from the group consisting of polyurethane, polyvinyl chloride, polyethylene terephthalate, polyethylene, polypropylene, polycarbonate, polytetrafluoroethylene and fluorinated ethylene polymer.

6. The process of claim 1, wherein the solution is coated on the portion in an amount so as to form a coating of the fatty acid diester of phosphatidyl choline in step b) of a thickness in the range 10–1000 nm.

7. The process of claim 1, wherein the device is a catheter.

8. The process of claim 7, wherein the catheter is a thoracic drain catheter.

9. The process of claim 1, wherein the fatty acid diester of phosphatidyl choline is selected from the group consisting of dipalmitoyl phosphatidyl choline, dimyristoyl phosphatidyl choline and fatty acid diesters of phosphatidyl choline extracted from egg yolk and from soya bean lecithin.

10. The process of claim 1, wherein the solvent comprises an alcohol selected from the group consisting of methanol, ethanol, iso-propanol and n-propanol.

11. A process for increasing the lubricity and reducing the thrombogenicity of a body tissue contacting surface of a single-use disposable device in which a portion of the surface of the device which is inserted into the body and contacts body tissue is subjected to the steps of:

a) coating of the portion with a solution consisting of 2–10 mg/ml of a fatty acid diester of phosphatidyl choline selected from the group consisting of dipalmitoyl phosphatidyl choline, dimyristoyl phosphatidyl choline and fatty acid diester phosphatidyl cholines extracted from egg yolk and soya bean lecithin in an organic solvent comprising an alcohol selected from the group consisting of methanol, ethanol, iso-propanol and n-propanol; and b) removing the organic solvent to form a coating of the fatty acid diester of phosphatidyl choline physically adsorbed and retained on the portion by hydrophobic interaction, whereby the lubricity of the portion is increased and the thrombogenicity of the portion is decreased compared to an uncoated device.

12. A process for increasing the lubricity and reducing the thrombogenicity of a body tissue contacting surface of a single-use disposable catheter device in which a portion of the surface of the catheter which is inserted into the body and contacts body tissue is formed of a plastic material selected from the group consisting of polyurethane, polyvinyl chloride, polyethylene terephthalate, polyethylene, polypropylene, polycarbonate, polytetrafluoroethylene and fluorinated ethylene polymers and is subjected to the steps of:

a) coating of the portion with a solution of a fatty acid diester of phosphatidyl choline selected from the group consisting of dipalmitoyl phosphatidyl choline, dimyristoyl phosphatidyl choline extracts of egg yolk and soya bean lecithin in an organic solvent comprising an alcohol selected from the group consisting of methanol, ethanol, iso-propanol and n-propanol;

b) and removing the organic solvent to form a coating of the fatty acid diester of phosphatidyl choline physically adsorbed and retained on the portion by hydrophobic interaction, whereby the lubricity of the portion is increased and the thrombogenicity of the portion is decreased compared to an uncoated device.

13. A process for increasing the lubricity and reducing the thrombogenicity of a body tissue contacting surface of a single-use disposable device in which a portion of the surface of the device which is inserted into the body and contacts body tissue is formed of a plastic material selected from the group consisting of polyurethane, polyvinyl chloride, polyethylene terephthalate, polyethylene, polypropylene, polycarbonate, polytetrafluoroethylene and fluorinated ethylene polymers and is subjected to a coating process consisting of the steps of:

a) coating of the portion with a solution consisting of a fatty acid diester of phosphatidyl choline selected from the group consisting of dipalmitoyl phosphatidyl choline, dimyristoyl phosphatidyl choline and fatty acid diesters of phosphatidyl choline extracted from egg yolk and soya bean lecithin, and an organic solvent; and b) removing the organic solvent to form a coating of the fatty acid diester of phosphatidyl choline physically adsorbed and retained on the portion by hydrophobic interaction, whereby the lubricity of the portion is increased and the thrombogenicity of the portion is decreased compared to an uncoated device.

* * * * *